United States Patent [19]

Crippen et al.

[11] Patent Number: 5,496,566
[45] Date of Patent: Mar. 5, 1996

[54] TECHNIQUE FOR COMBATTING UNDESIRED EMF/ELF

[76] Inventors: Raymond C. Crippen, 614 Loveville Rd. Apt. D2G, Hockessin, Del. 19707; Carleton T. Miller, Stewart Rd., Box 840, Rd. #1, Woodstown, N.J. 08098

[21] Appl. No.: 277,508

[22] Filed: Jul. 19, 1994

Related U.S. Application Data

[63] Continuation of Ser. No. 27,470, Mar. 8, 1993, abandoned, which is a continuation-in-part of Ser. No. 847,685, Mar. 6, 1992, abandoned.

[51] Int. Cl.[6] ................ A01N 59/00; A01N 59/06
[52] U.S. Cl. ................ 424/687; 424/600; 424/682; 424/686; 424/688; 424/689; 424/692; 424/693; 424/715; 424/722
[58] Field of Search ................ 424/600, 686, 424/688, 689, 682, 687, 692, 693, 715, 722

[56] References Cited

PUBLICATIONS

Kirschvink, Joseph L. "A Cautionary Note on Magnetoreception in Dowsers", in: Kirschvink, Joseph L. et al. (Eds.) Magnetite Biomineralization and Magnetoreception in Organisms, Plenum Press, N.Y., 1985, pp. 609–610.
Pool, R. "Flying Blind: The Making of EMF Policy", Science, vol. 250 (Oct. 5, 1990), pp. 23–25.
Miall's Dictionary of Chemistry, 5th ed. Great Britain, Longman Group Limited, 1981 p. 7.

*Primary Examiner*—Richard L. Raymond
*Assistant Examiner*—John D. Pak

[57] ABSTRACT

A method of installing in a building a suspension containing paramagnetic susceptible elements consisting essentially of:

(A) providing in a non-metallic container 5–12 pounds of a composition consisting essentially of (i) 30–99 wt % of a carbonate or a mixture of two or more carbonates selected from the group consisting of magnesium carbonate, calcium carbonate, strontium carbonate, barium carbonate and mixtures thereof, wherein the carbonate or mixture of carbonates are in powder form, (ii) 1–70 wt % of activated carbon in powder form, (iii) 0.1–10 wt % of an oxide or hydroxide additive in powder form;

(B) adding –2 gallons ml of water to the non-metallic container to form a suspension in water;

(C) placing said non-metallic container in a building;

(D) providing two electrically conductive wires;

(E) inserting a bare portion of one electrically conductive wire into the non-metallic container to make contact with the suspension, and making a ground connection with the opposite end of the wire; and (F) inserting a bare portion of the remaining electrically conductive wire into the non-metallic container to make contact with the suspension, and making a connection to a water pipe in the building with the opposite end of the wire.

5 Claims, 1 Drawing Sheet

TECHNIQUE FOR COMBATTING UNDESIRED EMF/ELF

CROSS-REFERENCE TO RELATED APPLICATION

This application is a continuation of application Ser. No. 08/027,470, filed Mar. 8, 1993, which is now abandoned, which in turn is a continuation in part of application Ser. No. 847,685 filed Mar. 6, 1992, which is now abandoned.

BACKGROUND OF INVENTION

There has been a growing awareness that electromagnetic forces (EMF) particularly extra-low frequency (ELF) have caused various problems including health hazards. Growing evidence has linked these forces with a wide variety of environmental problems including in humans and in animals. The literature is replete with concern over these problems including detrimental effects resulting from microwave radiation, power lines, electric blankets, computer terminals and various household appliances. Recent concern has been expressed with respect to the dangers of cellular telephones and with various studies which have linked exposure to EMF to the higher than normal incidents of leukemia and cancers of the breast, prostate and brain.

It would desirable if some techniques could be developed which could combat these harmful EMF/ELF forces.

SUMMARY OF INVENTION

An object of this invention is to provide techniques for combatting undesired EMF/ELF.

A further object of this invention is to provide such techniques which could have environmental applications.

In accordance with this invention a composition is provided by admixing Period IIa elements as carbonates or limestone with activated carbon and sensitized with small amounts of oxides or hydroxides selected from the group consisting of the same Period IIa elements and the Period I elements Li, Na, K, Rb, Cs and Fr.

In a preferred practice of the invention the Period IIa carbonates are present in the admixture in a range of about 65–99% with the activated carbon being present in a range of 1–35%. The components are preferably in powdered form, in suspension or in contact with water.

When used for environmental purposes, the composition is placed in solution in a container. A pair of electrically conductive wires is disposed with one end of each wire in the solution. The opposite ends of the wires are grounded.

DETAILED DESCRIPTION

Figure 1:
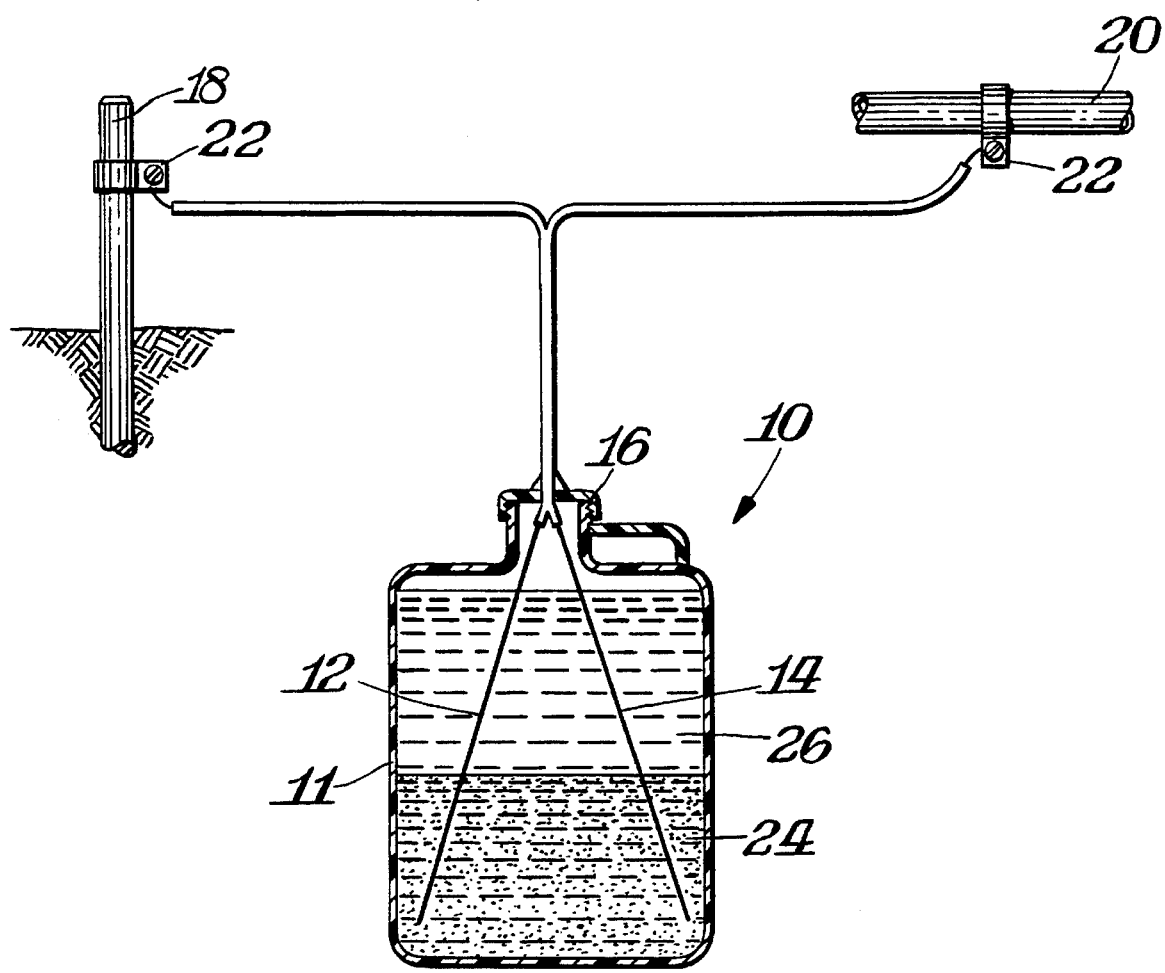
FIG. 1 shows in cross-section a device for practicing this invention in environmental applications.

The invention is based on the discovery that the Period IIa elements, as described below, as carbonates or limestone in admixture with certain grades of activated charcoal (carbon) and sensitized with small amounts of oxides or hydroxides of the same Period IIa elements, or in the case of the environmentally safe device, certain Period Ia elements, in suspension in water are capable of rendering beneficial properties from magnetic and environmental problems to all life which they come in contact or under which they have an influence, which will be described.

To sensitize these mixtures to enable them to absorb the electromagnetic energy (EMF extra-low frequency (ELF)) that may impinge on humans or animals, small amounts of the hydroxide or oxide of the Period IIa elements are used. The quantities vary with the degree of magnetic absorptive properties desired. Usually it varies from 0.1% to 1.0% or even up to 10% or more, where heavy magnetic environments are encountered.

The elements of the Period IIa of the Periodic Table comprise: beryllium, magnesium, calcium, strontium, barium and radium. The first and last members of this group are less representative of the group. For example, in the magnetic susceptibility properties, beryllium is diamagnetic, whereas the balance of the group (i.e. magnesium, calcium, strontium and barium) is paramagnetic. Radium is so radioactive that its magnetic properties are not generally known. Moreover, radium was also too dangerous to be used for the applications involved in this invention. The beryllium was too toxic as well as not having the right magnetic properties and thus is also not included in this invention.

Due to the similarity in magnetic susceptibility of the Period IIa elements, the Period Ia elements behave in a similar manner in this invention. The similarity of the magnetic susceptibility of the Period Ia elements such as lithium, sodium, potassium, rubidium, cesium and francium suggests the possibilities of using these as partial replacement for a portion of Period IIa elements. However, due to the extreme alkalinity of the carbonates, hydroxides and oxides of these elements, they cannot be used in contact with living tissue. The Period Ia elements, however, can be used in the environmentally safe device practice of this invention as later described.

Pure limestone or other Period IIa elements as carbonate alone has little or no magnetic properties unless sensitized as later described. However, it does not have organic absorption properties unless the carbon is added. Both of these properties, either singly or collectively, are the basis of this invention.

Using small amounts of these mixtures suspended in water, such as 10–15 g. in 100–250 ml. water, the magnetic properties were measured. It was found that all of the Period IIa elements, as carbonates, in admixture with certain grades of activated carbon and sensitized as described above, showed positive electro-magnetic properties.

The invention is not intended to provide a cure for medical ailments, for example, but rather to combat the undesired or detrimental effects of EMF/ELF. It is not completely understood how the invention works, but it is believed that the mixture used in the invention functions to absorb the EMF/ELF.

The invention is effective without necessarily absorbing the EMF radiation emanating from electrical systems. A gaussmeter could be used to measure this radiation. The intent of the invention, however, is to absorb the ELF radiation component of the EMF radiation that could affect health and other environmental conditions.

The device which incorporates the invention has been developed to absorb the ELF fraction of the EMF that affects the health and well-being whether in homes, offices, businesses, industries, schools and even outdoors. Each environment is different and the extent to which the invention must be used could vary for different environments. In some instances the initial magnetic properties might be such that only one device using the invention is adequate to perform its function while other conditions might require multiple devices.

Although the above described techniques are useful in providing one manner of obtaining comparative magnetic properties, it is to be understood that the invention may be practiced using more sophisticated equipment or even cruder equipment which would provide some comparison of the magnetic properties before and after use of the invention.

Attempts to replace the Period IIa elements with Period Ia elements, as carbonates, or with Period IIa elements gave erratic results. Only when a minute portion was replaced and the pH maintained around 8–9, could more reliable results be obtained. Attempts to replace the activated carbon with other grades or forms of carbon, such as lampblack and pulverized coke, showed little or no positive electromagnetic properties in these mixtures. Replacement of the carbon with finely powdered pure silicon, phosphorus or other similar elements also showed erratic or none of the desired electro-magnetic properties. Silicon did give positive magnetic properties, but on long standing the silicon dissolved in the alkaline solution.

It has been also found that the Period IIa elements as carbonates, were most active in the region of 65% to 99% and preferably 70% to 99%, weak from 30% to around 60% and poor at 1% to 20% with the balance being the activated carbon. Similarly, the carbon concentration was varied from 2% to 95% with the higher concentrations of carbon being less effective such as 80% to 99%, medium ranges being somewhat effective at 40% to 70%, with the most effective range in the lower concentration of carbon at 1% to 35%.

Activated carbons (charcoal) made from hard woods, lignites, coconut, nutshells or other hard nut carbons, and other hard carbohydrates containing organic materials converted to carbons were most effective. Those made from soft woods, cotton, soft bio-mass materials, petroleum chars and cokes, coal chars and cokes, bone chars and from coal and other bio-mass materials that yield carbons with wide pores were less effective or even ineffective. Graphite carbons and carbons made from burning petroleum in limited access to air to form lampblack and other carbon blacks of similar composition were ineffective.

All components in this invention are in powdered form, in suspension, or in contact with water. When these powders were compressed into a mass or allowed to settle into a hard mass they became less effective especially so in the later described environmental device. It was also found that the components of these mixtures, when tested individually, did not have the properties desired with this invention. Also when these components were in a dry state they showed little or no activity as far as this invention is concerned.

The use of suspending agents helps the activity for a much longer period. Any suitable suspending agent may be used such as the agricultural suspending agent Activator 90 made by Loveland Industries of Greeley Co. Also when the activity of the later described environmental device seemed to be reduced, it was noted that either: (1) the components had become compacted and needed resuspension or (2) the contacting connection had become loose or corrosion had interfered and needed to be cleaned to make a good contact.

USE APPLICATION OF INVENTION

1. Agricultural Applications: Due to the toxicity of strontium and barium, only the magnesium and calcium mixtures were used. Most of the above noted ranges of concentration could be used, but the most effective and cost effective were those made from limestone, sensitized as described above and the grades of activated carbon also described above. These mixtures are not used to replace any fertilizer, but to augment the fertilizer uses. The most effective range was 95 to 98% sensitized limestone and balance being active carbon. These mixtures are suspended in water and are sprayed on plants or around and in the soil on which plants are growing or are to be grown. These mixtures can even be dusted on the seeds just prior to planting. The carbon acts to absorb the toxins such as pesticides, herbicides and other chemicals that may be affecting the plants. The plants are then adjusted into their proper magnetic environment to flourish and grow vigorously.

The mixtures for spraying or dusting on plants, on soil, on seeds to be planted, etc., comprises the above mixtures in the ranges of 1% to 5% carbon or higher for highly polluted areas and the 95% to 99% balance sensitized limestone as described above. These mixtures can be administered along with fertilizers but not in place of fertilizers.

The concentration used in these applications varies widely, depending upon the pollution of the growing area with pesticides, herbicides and other toxins that may be inhibiting the plants' growth. Usually it ranges from 2–3 lbs. per acre to more than 10–15 lbs. per acre depending upon the pollution factors. Both the plants and the soil can be tested for their proper magnetic environment. This will show up in increased yields and more healthy looking crops.

2. Animal Applications: Using mixtures of calcium/magnesium such as in limestone, sensitized as above, and active carbons as described above, in the ranges from 95% to 99% limestone, and the balance carbon are admixed with the feed of animals. Such range is preferable if animals are badly contaminated with pesticides, herbicides or other pollutants. The mixture should be adjusted so that each animal ingests from 1 to 3 oz. per day for large animals (such as cows, horses, etc.) or ¼ oz. to 1 oz. per day for smaller animals (such as hogs, goats, sheep, large dogs or other domesticated animals). The small animals (such as chickens, cats, small dogs, etc.) should have lower amounts added to their food.

Using these mixtures on dairy cattle, it was found that the incidence of mastitis and other disorders could be reduced or even eliminated. The animal appeared better, was less "jumpy" and milk production increased with no trace of pesticides, herbicides or the afflatoxins that may have been in the feeds. The animals' magnetic environment was also improved.

One interesting observation concerning this investigation was that herds of dairy cows on this treatment were less subject to excess flies. The flies laid their eggs on the animals fecal matter, the eggs did hatch, however the larvae did not mature into adult flies. The carbon in the fecal matter was still absorbing the maturing hormone of the larvae.

Another interesting observation using human size dietary aid capsules on adult female dogs or cats during estrus cycle, it was noted that these females did not have an off-spring until sometime after the treatment was discontinued. They then had their normal offspring with no deleterious effects. The carbon evidently absorbed one of the hormones that produced the estrus cycle.

The treatment has been tried on calves, but extreme care must be exercised to prevent anemia. Too high levels of carbon usage would produce anemia in some new born calves. However, it was noted in feeding to fattening cattle that there was less fat on the carcass, but the cattle gained weight faster with less consumption of feed. In place of the fat there was more lean meat. All animals appeared well and healthy with weight gain above normal of that of untreated animals.

3. Environmental Application: This use of the invention is of particular importance since it dramatically demonstrates the diverse benefits obtained from the same or similar compositions of matter. In all applications previously and later described the same principles are used: 1. absorptive properties of carbon, and 2. magnetic environment adjustment properties of the sensitized carbonates. All of these benefits are obtained from these ingredients only.

The following description shows the environmental benefits. Mixtures from the Period IIa elements, excluding beryllium and radium, from 1% up to 99% can be used in this invention, with the balance being activated carbon. The mixtures are sensitized as described above.

As shown in FIG. 1 an electro-magnetic absortive device 10 includes a container 11. Approximately 5 to 12 lbs. of a mixture having 95–98 wt % limestone, sensitized as described above, with the balance activated carbon, acted as an EMF (ELF) absorber when placed in the non-metallic (such as a plastic) container 11. The container capacity can be approximately two gallons for homes. Five to ten lbs. or more of these mixtures are suspended in water in a 2 gallon plastic container 11. Smaller containers, such as pint and quart units, have also been found very effective around electronic equipment in protecting from EMF (ELF) radiation.

The containers 11 are filled with good quality water 26. Two lengths of #10 electrically conductive copper wire (larger or smaller gauge) 12, 14 are stripped of insulation inside the container 11. The insulated section of wires 12, 14 is projected outside the container 11 through the cap 16. The lower portion of the wires 12, 14 are stripped bare inside the container 11. The balance of the wires, as required is attached to: (1) the electrical ground 18 of the electric system; and (2) the hot/cold water line 20 with metal connectors 22. Good connections are essential as both wire connections must be carefully cleaned as well as the connections to water pipe and electric ground and protected from corrosion. The cap 16 is closed and sealed to prevent loss of water. The good suspension agent can be added to prevent hard settling. As shown, the sensitized Period IIa elements as carbonates, plus 1% to 5% carbon are in the bottom of container 11 with the water 26 being filled near the container top.

By attaching the device 10 to the ground 18 of the electrical system and the hot or cold water line 20 through suitable clamps 22, a large area around the device 10 is protected from electro-magnetic radiation. This combats EMF/ELF that may be absorbed by persons or animals within the area.

Small amounts of Period Ia elements such as lithium, sodium, potassium, cesium and rubidium are effective as a partial replacement as carbonates. However, from tests only the potassium as a carbonate is completely effective as a full replacement.

The environmental electromagnetic absorption device 10, when properly installed in a home, business office, or industrial facility will absorb the EMF (electromagnetic force energy-ELF) extra-low frequency radiation that can affect the health, well-being or welfare of individuals or animals living within its influence. Upon disconnecting the device 10, the absorption effect disappears.

The carbon in this invention, acts as a powerful organic absorber as well as a magnetic environment adjuster. It can absorb toxins, unwanted metabolites, by-products, pesticides, herbicides and other pollutants up to 30 to 40 times its own weight.

In installing a device of this invention, such as device 10 the effective grounding of the wires should be made. The slightest corrosion on the ground wires, a break in the existing ground, or even for example, inadequate grounding will affect the performance of the devices. Even the corrosion on the battery cable on an automobile ground will affect the performance. When a device is used in a building one of the wires could be grounded by being connected to the fuse box. The other wire could also be grounded in any suitable manner, such as being connected to a water pipe.

Various combinations which form the mixture used in the invention include the following: activated charcoal and limestone, wherein the limestone is treated by incorporation of slaked or lime; activated charcoal and magnesium carbonate wherein the magnesium carbonate is treated with milk of magnesia or magnesium oxide; activated charcoal and strontium carbonate with the carbonate being treated with strontium hydroxide or strontium oxide; activated charcoal and barium carbonate with the carbonate treated with barium hydroxide or barium oxide or the above mixtures wherein the magnetic properties are enhanced by incorporation of hydroxides of sodium or potassium or lithium or cesium or rubidium.

The limestone or other Period IIa elements as carbonates, sensitized as described above, regulates the magnetic environment so that the plant, animal or human is placed under a more favorable magnetic environment. The material in the magnetic absorption device then absorbs the excess EMF (ELF) energy to correct the magnetic environment of animals, humans and plants living within its influence.

What is claimed is:

1. A method of installing in a building a suspension containing paramagnetic susceptible elements consisting essentially of:

(A) providing in a non-metallic container a composition consisting essentially of (i) 30–99 wt % of a carbonate or a mixture of two or more carbonates selected from the group consisting of magnesium carbonate, calcium carbonate, strontium carbonate, barium carbonate and mixtures thereof, wherein the carbonate or mixture of carbonates are in powder form, (ii) 1–70 wt % of activated carbon in powder form, (iii) 0.1–10 wt % of an additive selected from the group consisting of magnesium oxide, magnesium hydroxide, calcium oxide, calcium hydroxide, strontium oxide, strontium hydroxide, lithium oxide, lithium hydroxide, sodium oxide, sodium hydroxide, potassium oxide, potassium hydroxide, rubidium oxide, rubidium hydroxide, cesium oxide, cesium hydroxide and mixtures thereof, wherein the additive is in powder form;

(B) adding water to the non-metallic container to form a suspension in water, wherein the proportion of the composition to the added water is 5–12 lbs of the composition per 2 gallons of water;

(C) placing said non-metallic container in a building;

(D) providing two electrically conductive wires;

(E) inserting a bare portion of one electrically conductive wire into the non-metallic container to make contact with the suspension, and making a ground connection with the opposite end of the wire; and (F) inserting a bare portion of the remaining conductive wire into the non-metallic container to make contact with the suspension, and making a connection to a water pipe in the building with the opposite end of the wire.

2. The method of claim 1 wherein 70–90 wt % of carbonate or mixture of carbonates is present in the composition.

3. The method of claim 1 wherein the additive is selected from the group consisting of lithium oxide, lithium hydroxide, sodium oxide, sodium hydroxide, potassium oxide, potassium hydroxide, rubidium oxide, rubidium hydroxide, cesium oxide, cesium hydroxide, and mixtures thereof, and the pH of the suspension is 8–9.

4. The method of claim 1 wherein 1–5 wt % of activated carbon and 95–99 wt % of limestone in admixture with slaked lime are present in the composition.

5. The method of claim 1 wherein 65–99 wt % of a carbonate or a mixture of two or more carbonates and 1–35 wt % of activated carbon are present in the composition.

* * * * *